United States Patent [19]

Sliski et al.

[11] Patent Number: 5,635,709
[45] Date of Patent: Jun. 3, 1997

[54] METHOD AND APPARATUS FOR MEASURING RADIATION DOSE DISTRIBUTION

[75] Inventors: Alan P. Sliski, Lincoln; Michael Dalterio, Sudbury; Donald O. Smith, Lexington, all of Mass.

[73] Assignee: Photoelectron Corporation, Waltham, Mass.

[21] Appl. No.: 542,066

[22] Filed: Oct. 12, 1995

[51] Int. Cl.$^6$ .................................................. G01D 18/00
[52] U.S. Cl. ........................ 250/252.1; 378/207; 378/18
[58] Field of Search .................. 378/207, 18; 250/252.1, 250/336.1, 370.07; 128/653.1; 606/130

[56] References Cited

U.S. PATENT DOCUMENTS

| | | | |
|---|---|---|---|
| 4,300,050 | 11/1981 | Hizo et al. | 250/252.1 R |
| 4,406,947 | 9/1983 | Burton et al. | 250/252.1 R |
| 5,006,714 | 4/1991 | Attix | 250/252.1 R |
| 5,153,900 | 10/1992 | Nomikos et al. | |
| 5,369,679 | 11/1994 | Sliski et al. | |
| 5,430,308 | 7/1995 | Feichtner et al. | 378/207 |
| 5,511,107 | 4/1996 | Sliski | 378/207 |
| 5,511,549 | 4/1996 | Legg et al. | 128/653.1 |

*Primary Examiner*—Brian L. Casler
*Attorney, Agent, or Firm*—Lappin & Kusmer LLP

[57] ABSTRACT

A phantom apparatus for measuring the radiation dose distribution produced by a brachytherapy device used to treat a localized area with radiation. The brachytherapy device includes an insertable probe capable of producing predefined radiation dose geometries about a predefined point. The phantom apparatus includes a tank containing a medium having a radiological equivalent characteristic of the localized area to be treated. The phantom apparatus also includes a radiation sensor for measuring the radiation dose and a positioning system for moving the probe with respect to the radiation sensor. The radiation sensor is also coupled to a positioning system to orient the sensor for optimal dose measurements. The phantom apparatus includes a control system that coordinates the movements of the probe and the radiation sensor to avoid a collision. The control system moves the probe along a predefined path around radiation sensor and records the dose at predefined points along the path. In order to reduce the settling time of the sensor, the path is selected to coincide with the isodose contours of the radiation dose distribution of the probe.

20 Claims, 10 Drawing Sheets

METHOD AND APPARATUS FOR MEASURING RADIATION DOSE DISTRIBUTION

BACKGROUND OF THE INVENTION

This invention relates to a method and apparatus for measuring the radiation dose distribution produced by a radiation source. Specifically, the invention is directed to a method and apparatus for measuring the radiation dose distribution produced by a radiation source which produces radiation in predefined patterns disposed about a central location.

In the field of medicine, radiation is used for diagnostic, therapeutic and palliative treatment of patients. The conventional medical radiation sources used for these treatments include large fixed position machines as well as small, transportable radiation generating probes. The current state of the art treatment systems utilize computers to generate complex treatment plans that require verification to insure proper treatment.

In order to be able to more precisely provide a desired dose and volume of treatment, it is necessary to calibrate the radiation source by accurately measuring the radiation pattern of the source. Since the radiation dose is affected by the density of the irradiated volume, the more dense the material, the more radiation it will absorb, it is desirable to model the volume to be irradiated, and to conduct the calibration procedure on such a model. It is also desirable to perform the treatment plan in such a model, and confirm that the desired radiation dose distribution is being produced.

Conventional radiation treatments systems, such as the LINAC used for medical treatment, utilize a high power remote radiation source and direct a beam of radiation at a target area, such as tumor inside the body of a patient. This type of treatment is referred to as teletherapy because the radiation source is located a predefined distance, approximately one meter, from the target. This treatment suffers from the disadvantage that tissue disposed between the radiation source and the target is exposed to radiation.

Prior to treatment, the teletherapy system is calibrated using an ionization chamber positioned generally along the beam path but distant from the radiation source. The ionization chamber is disposed within a large tank of water, hereinafter referred to as a water phantom. The water in the water phantom approximates the radiation density of living tissue and simulates the body of the patient. During calibration, the ionization chamber is moved within the water phantom and the system accumulates individual radiation dose measurements at predetermined points in the water phantom. The individual dose measurements are utilized to construct a three dimensional dose distribution for the calibration pattern and/or radiation treatment applied.

An alternative treatment system utilizing a point source of radiation is disclosed in U.S. Pat. No. 5,153,900, owned by the assignee of the present application. The system includes a miniaturized, insertable probe capable of producing low power radiation in predefined dose geometries disposed about a predetermined location. This treatment is referred to as brachytherapy because the source is located close to or in some cases within the area receiving treatment. One advantage of brachytherapy is that the radiation is applied primarily to the treatment volume, without significantly affecting the tissue in adjacent volumes.

Prior to treatment, the brachytherapy system must also be calibrated to verify the radiation dose distribution. Conventional water phantoms/ionization chamber calibration techniques are not effective in measuring the dose distribution of the brachytherapy system because there is no way to orient the ionization chamber to keep it pointed at the radiation source for various points within the phantom. It is necessary to orient the ionization chamber in order to obtain high resolution dose measurements. In addition, since brachytherapy is applied only to near-source tissue, the ionization chamber must be very close to the radiation source, typically less than 5 centimeters, and therefore, the movements of the ionization chamber must be controlled to avoid colliding with the probe.

Accordingly, it is an object of the invention to provide a method and apparatus for measuring the dose distribution about a source of radiation.

It is another object of the invention to provide a method and apparatus for measuring the radiation dose distribution about a source at one or more points in the target volume.

It is another object of the invention to provide an apparatus for measuring the radiation dose distribution about a source which can orient the radiation measuring element toward the source.

It is yet another object of the invention to provide an apparatus for measuring the radiation output of a source which is capable of moving the source with respect to the radiation measuring element and which is capable of avoiding a collision between the source and the radiation measuring element.

SUMMARY OF THE INVENTION

The invention relates to a phantom apparatus for use in calibrating a brachytherapy device such as the Miniaturized Low Power X-ray Source disclosed in U.S. Pat. No. 5,153,900. This low power radiation source includes a housing and an elongated probe extending from the housing along a probe axis to a distal end. The device is capable of producing low power radiation in a wide range of predefined dose distribution geometries about the distal end of the probe. In some forms, the source may behave substantially as a point source, generating radiation which propagates substantially omnidirectionally from a small volume or point of the distal end. Alternatively, the source may generate some other radiation pattern.

The phantom apparatus includes a tank or enclosure containing a medium that is the radiological absorption equivalent of the volume to be treated with radiation. By way of example, that medium may be water. The phantom apparatus also includes a radiation measuring element for measuring the radiation dose at one or more predetermined locations in the medium contained in the phantom apparatus and a positioning system which supports and positions the probe within the medium with respect to the radiation measuring element. A control system establishes relative motion of the source in a predefined path to predefined positions with respect to the radiation measuring element. The control system records the dose measured by the radiation measuring element for each predetermined position and uses this data to produce two and three dimensional representations of the radiation dose distribution.

In order to obtain precise radiation dose measurements, it may be necessary to orient the radiation measuring element to be in alignment with the radiation propagating from the source. The radiation measuring element can be coupled to a positioning system in order to permit the orientation of the radiation measuring element to be adjusted for optimum measurement of the radiation dose. In this respect, the control system can also control the position and orientation of the radiation measuring element as well as coordinate the movements of the radiation source and the radiation measuring element to avoid a collision between them. The control system compares the path of the radiation source with the location of the radiation measuring element to determine if they intersect or come within a predetermined unsafe distance of each other. If a collision is determined, the control system plots a corrected path to avoid a collision. Alternatively, the control system can nest movements according to a polar coordinate system to avoid a collision.

The control system moves the probe to predefined positions along a predefined path and moves the radiation measuring element to be aligned with the incident radiation to obtain precise radiation measurements. The control system adjusts the path of the probe to avoid a collision with the radiation measuring element. In determining the path from one point to another, the control system can determine a path which maintains the probe at a substantially constant distance from the radiation measuring element in order to reduce the settling time of the radiation measuring element. In the instance where the expected dose distribution is nonsymmetrical around the distal end of the probe, the control system can determine a path along the isodose contours of the expected radiation dose distribution to reduce the settling time of the radiation measuring element.

In one form, the phantom apparatus includes a top cover having a radiation shield assembly which permits the probe to be inserted through the top cover and moved horizontally and vertically while limiting the escape of radiation through the top cover to safe levels. The shield assembly includes a cover plate having a transverse slot and a shield plate having an aperture of substantially the same cross sectional shape as the probe. The probe is inserted through the aperture in the shield plate and through the transverse slot in the top cover. The shield plate is coupled to the positioning system to move with the probe and is sufficiently large enough to cover the slot irrespective of the position of the probe in the slot and thereby preventing radiation from escaping through the slot.

In one embodiment, the probe is supported by a rigid cantilevered arm. The arm can be extended or contracted to align the probe axis with the radiation measuring element.

BRIEF DESCRIPTION OF THE DRAWINGS

The foregoing and other objects of this invention, the various features thereof, as well as the invention itself, may be more fully understood from the following description, when read together with the accompanying drawings in which.

DETAILED DESCRIPTION OF THE PREFERRED EMBODIMENTS

The present invention is a method and apparatus for measuring and determining the radiation dose distribution of a radiation source. In the preferred embodiment, the radiation source is an X-ray source in which an electron beam is directed along an elongated probe to a target at its distal end; in response to the incident elections, x-ray radiation is generated in a substantially omnidirectional pattern, thereby establishing a point source. Other x-ray source geometries and patterns may be used. The probe can be used for medical purposes, such as in the diagnostic, therapeutic and palliative treatment of patients. For purposes of illustration, the invention will be described in conjunction with a probe as used in the field of medicine. One of ordinary skill in the art will appreciate that the probe and the invention can be used in other fields where a controlled application of electromagnetic radiation is desirable.

Generally, the apparatus of the present invention includes a tank or enclosure defining an interior region for carrying a medium that is the radiological equivalent of the material being treated with radiation. In the illustrative example, water provides a suitable radiological equivalent medium for living tissue. The tank is adapted to receive an externally applied x-ray source such that the radiation-emitting distal end is within the tissue-equivalent medium.

A radiation measuring element is disposed at a central location in the medium. The radiation measuring element includes a radiation sensor capable of measuring the radiation dose applied to a location in the medium; generally the sensor has a preferred or sensing axis, along which incident radiation is measured.

The apparatus of the invention, also includes a system for positioning and orienting the radiation source with respect to the radiation measuring element and a system for positioning or orienting the radiation sensor with respect to a predetermined volume of the tissue-equivalent medium. A control system controls the positioning system for the radiation source and the positioning system for the radiation sensor. The control system coordinates the movements of the radiation source and the radiation sensor with respect to each other to maintain the sensing axis to be directed to the source, and also to avoid a collision between them during relative motion of those elements. The control system can also coordinate the movements of the radiation source and the radiation sensor during movements from one predefined position to the next in order to minimize the settling time of the radiation sensor.

Figure 1:
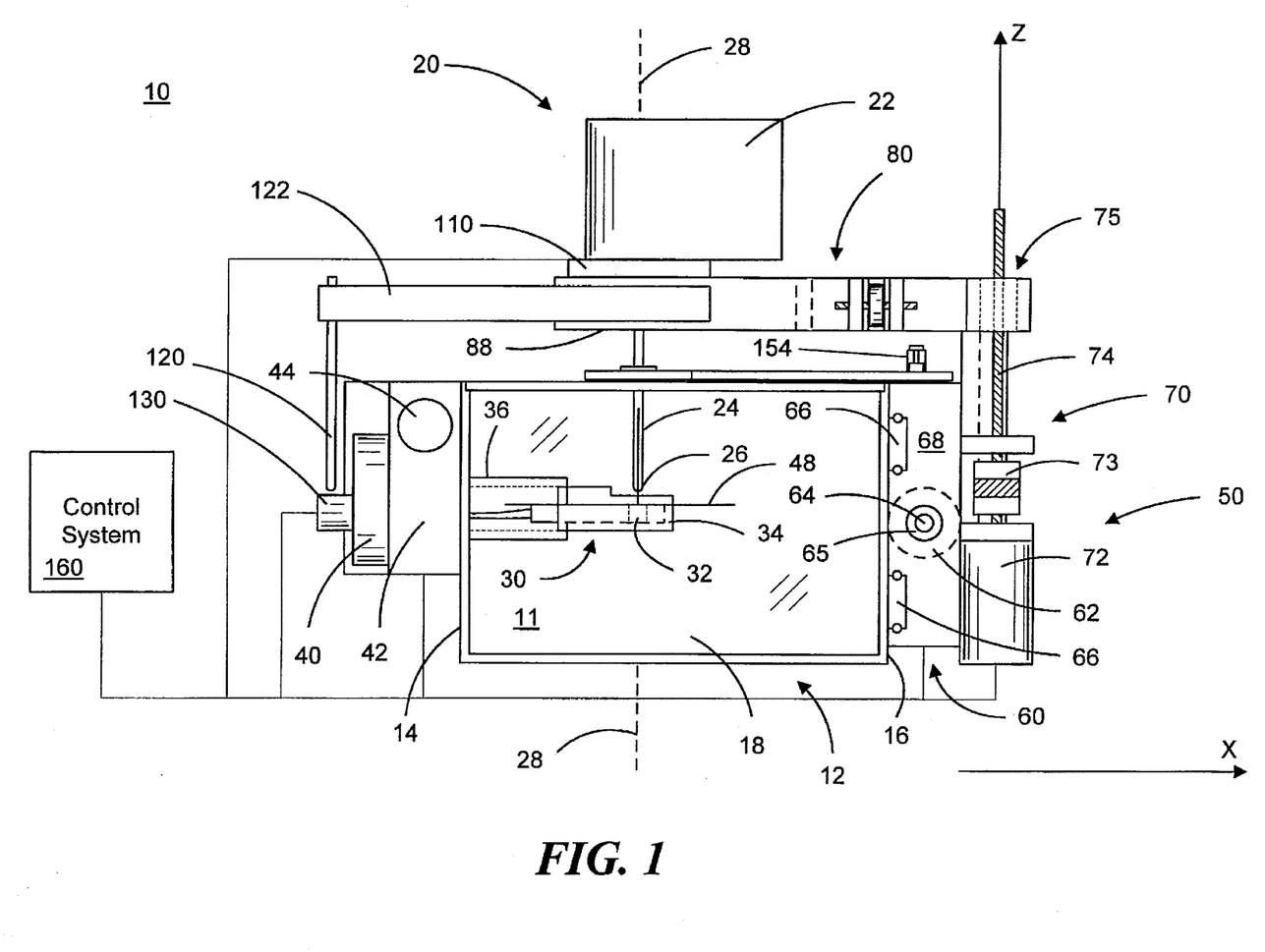
FIG. 1 is a front view of an apparatus for measuring the radiation dose distribution embodying the present invention.

FIG. 1 shows a radiation source 20 in combination with a phantom apparatus 10 embodying the present invention. The radiation source 20 includes an elongated probe 24 extending from a housing 22 along a probe axis 28. The radiation source 20 produces radiation in predefined dose distribution geometries about a point source 26 at the distal end of the elongated probe 24.

The phantom apparatus 10 includes a water-tight housing or tank 12 containing a volume of water 11 and a radiation measuring assembly 30 disposed in a central location inside the tank 12. The relative positions of the source 20 and sensor assembly 30 are controlled by various motor driven assemblies, described below, under the control of a controller 160.

Figure 2:
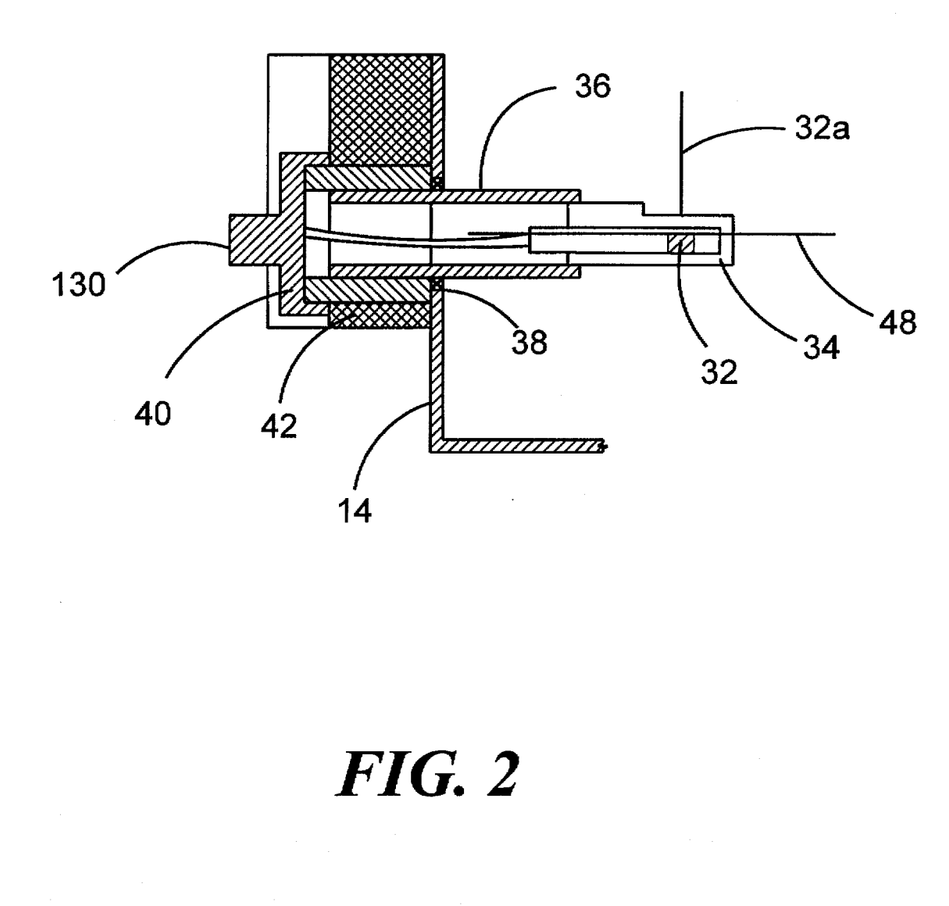
FIG. 2 is a detail view of the radiation measuring assembly of an apparatus for measuring the radiation dose distribution embodying the present invention.

As shown in FIG. 2, the radiation measuring assembly 30 includes a radiation sensor 32 mounted in an enclosure 34 disposed at that end of a tubular extension 36. The tubular extension 36 extends through an aperture in side wall 14 of the tank 12 and is coupled to the radiation sensor rotary actuator 42. The rotary actuator 42 enables the radiation measuring assembly 30 to be selectively rotated about an orientation axis 48. In the preferred embodiment, rotary actuator 42 includes a servomotor 44 controlled by the control system 160. The wire leads from the radiation sensor 32 extend through tubular extension 36, through aperture 35 and through a side cover 40 to the outside of the tank 12 where they are connected to the control system 160. A rotary seal 38 is provided to enable the tubular extension 36 to be rotated without the water leaking through the space between the tubular extension 36 and the aperture 35.

In the preferred embodiment, the radiation sensor 32 is an ionization chamber having a sensing axis 32a. The ionization chamber is capable of producing very precise measurements of radiation dose when the radiation propagates from the source along the sensing axis 32a to the ionization chamber. Because the ionization chamber is sensitive to ambient pressure and temperature, side cover 40 is vented to permit the ionization chamber 32 to be exposed to ambient pressure and temperature. Preferably, the enclosure 34 is constructed of a "Solid Water" material. "Solid Water" is plastic material designed to be the radiological equivalent of water for a given type of radiation. In the preferred embodiment where the radiation source generated x-ray radiation with energies up to 50 KeV, type 457 solid water is used. This material is available from Radiation Measurements, Inc. of Middleton, Wis.

A probe positioning system 50 is mounted to the side wall 16 of the tank 12 and moves the radiation source 20 with respect to the radiation sensor 32. The probe positioning system 50 includes a horizontal actuator 60, a vertical actuator 70 and a rotary actuator 110 to impart horizontal, vertical and rotary motion respectively to the radiation source 20. The control system 160 controls and coordinates the movements of the radiation source 20 with the movements of the radiation sensor 32.

Figure 3:
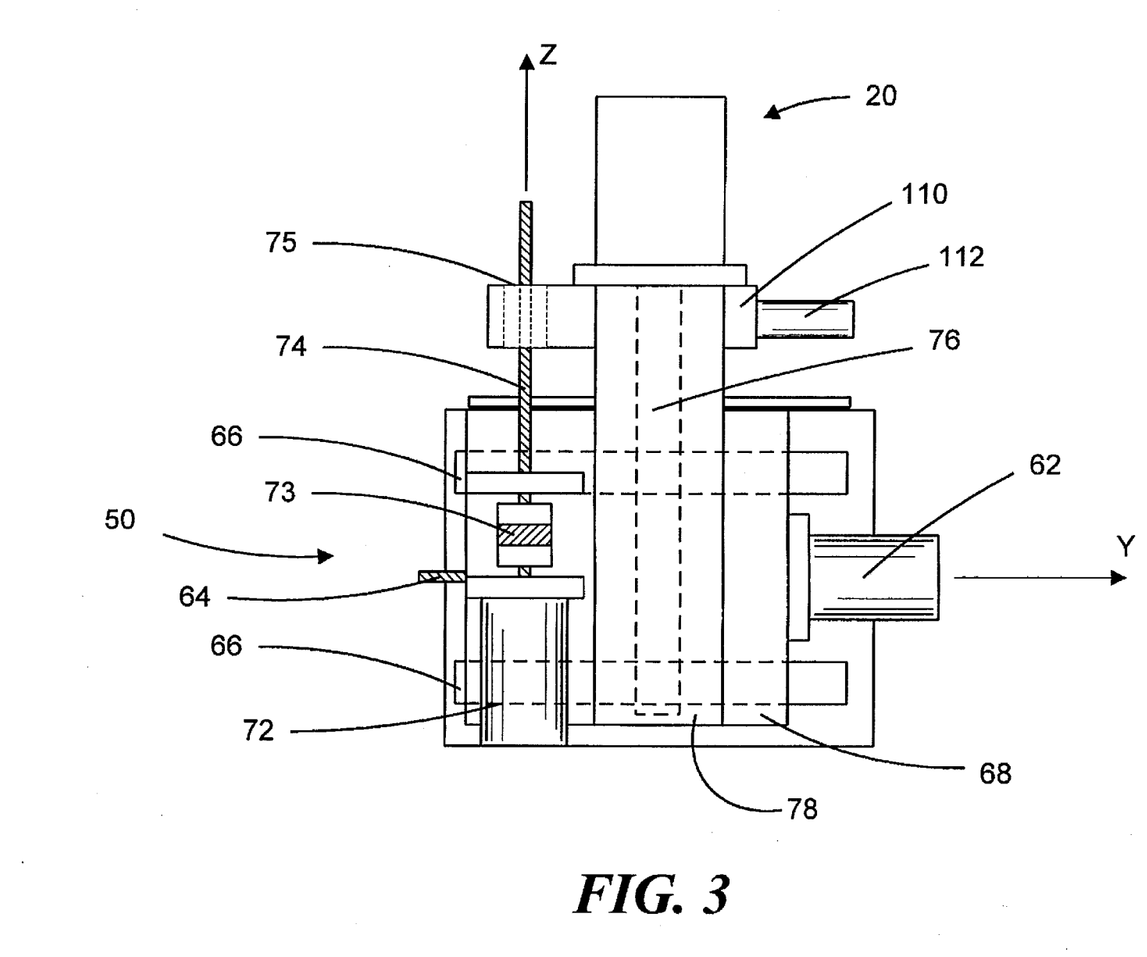
FIG. 3 is a right side view of an apparatus for measuring the radiation dose distribution embodying the present invention.

As shown in FIGS. 1 and 3, the horizontal actuator 60 includes a pair of elongated horizontal guides 66 secured to side wall 16 and a horizontal stage 68 engaging the horizontal guides 66 to control the horizontal movement of the horizontal stage 68 along a Y axis with respect to the tank 12. In the preferred embodiment, the elongated horizontal guides 66 include ball bearings which engage a track in horizontal stage 68 and provide virtually frictionless movement of the horizontal stage 68 in the horizontal direction and substantially prevent movement in any other direction. A horizontal actuator motor 62 is mounted to the side wall 16 and is coupled to a lead screw 64 by compliant coupling (not shown). The lead screw 64 engages drive nut 65 which is coupled to the horizontal stage 68 to move and position the horizontal stage 68 in the horizontal Y direction. In the preferred embodiment, the horizontal actuator motor 62 is a servomotor which is controlled by the control system 160.

As shown in FIGS. 1 and 3, the vertical actuator 70 includes a vertical guide 76 secured to the horizontal stage 68 and a vertical stage 78 engaging the vertical guide 76 to control the vertical (Z axis) movement of the vertical stage 78 with respect to the horizontal stage 68. In the preferred embodiment, the vertical guide 76 includes ball bearings which engage a track in the vertical stage 78 and provide virtually frictionless movement of the vertical stage 78 in the vertical direction and substantially prevent movement in any other direction with respect to the horizontal stage 68. A vertical actuator motor 72 is mounted to the horizontal stage 68 and coupled to a lead screw 74 by compliant coupling 73. The lead screw 74 engages drive nut 75 which is coupled to the vertical stage 78 to move and position the vertical stage 78 in the vertical direction along the Z axis, which is substantially parallel to the axis 28 of probe 24. In the preferred embodiment, the vertical actuator motor 72 is a servomotor which is controlled by the control system 160.

Figure 4:
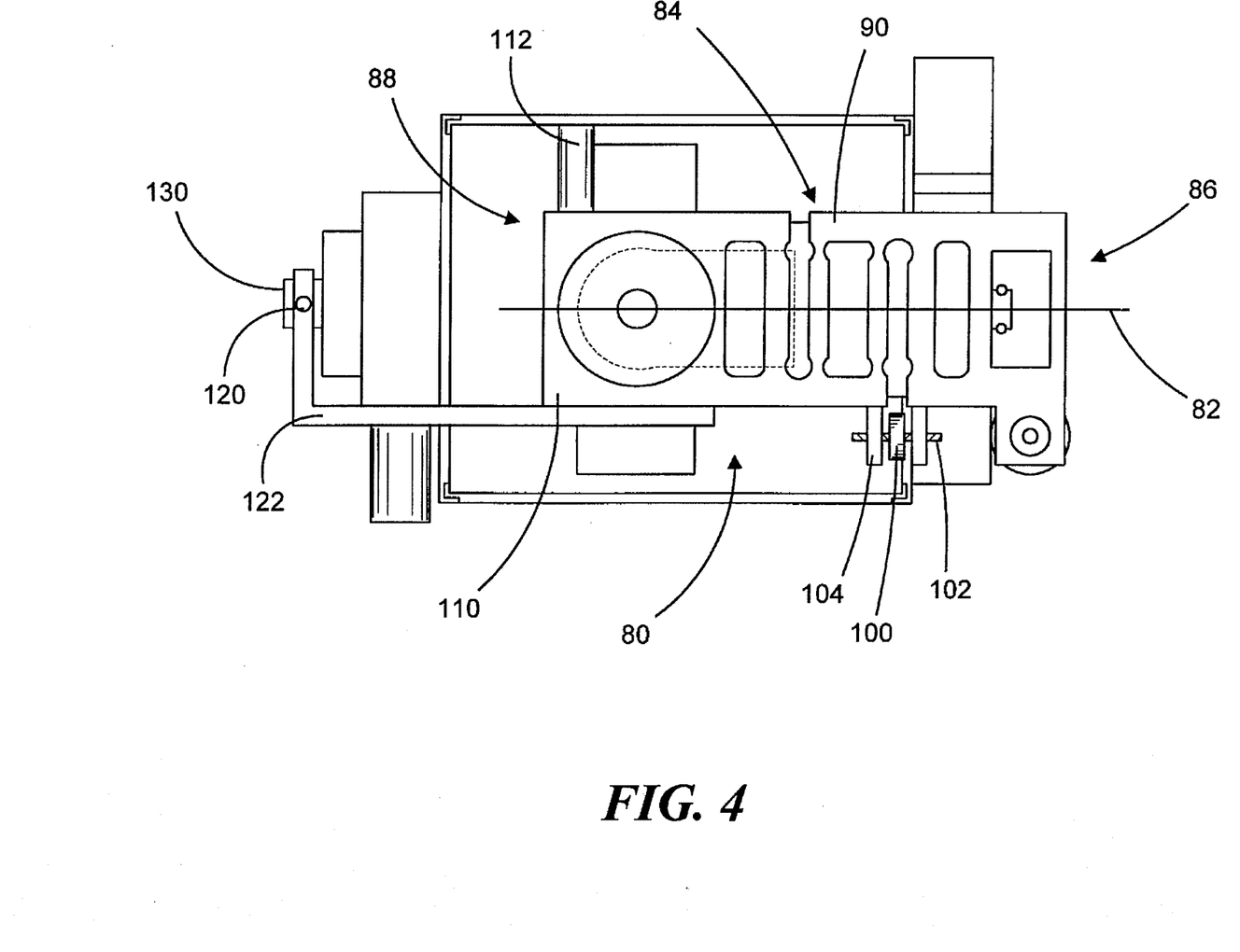
FIG. 4 is a top view of an apparatus for measuring the radiation dose distribution embodying the present invention.

As shown in FIGS. 1 and 4, a support arm 80 supports the actuator 110, as well as the source 20 positioned with its probe in tank 12. One end of the support arm 80 is coupled to the vertical stage 78 and extends cantilevered therefrom over the tank 12. Preferably, the support arm 80 extends in a direction substantially parallel to the orientation axis 48 and in a direction substantially orthogonal to the direction of motion of the horizontal stage 68 along the Y axis and the direction of motion of the vertical stage 78 along the Z axis. The support arm 80 also includes a radiation source rotary actuator 110 adjacent to the cantilevered or free end 88. The housing 22 of the radiation source 20 is mounted on the source rotary actuator 110 to permit rotary motion of the point source 26 about probe axis 28. The source rotary actuator 110 includes a servomotor 112 controlled by the control system 160 to establish such motion. Because the support arm 80 is coupled to vertical stage 78 which is mounted to horizontal stage 68, the phantom apparatus 10 provides for both X and Y horizontal motion and Z vertical movement of the radiation source 20 relative the sensor 32.

Figure 5:
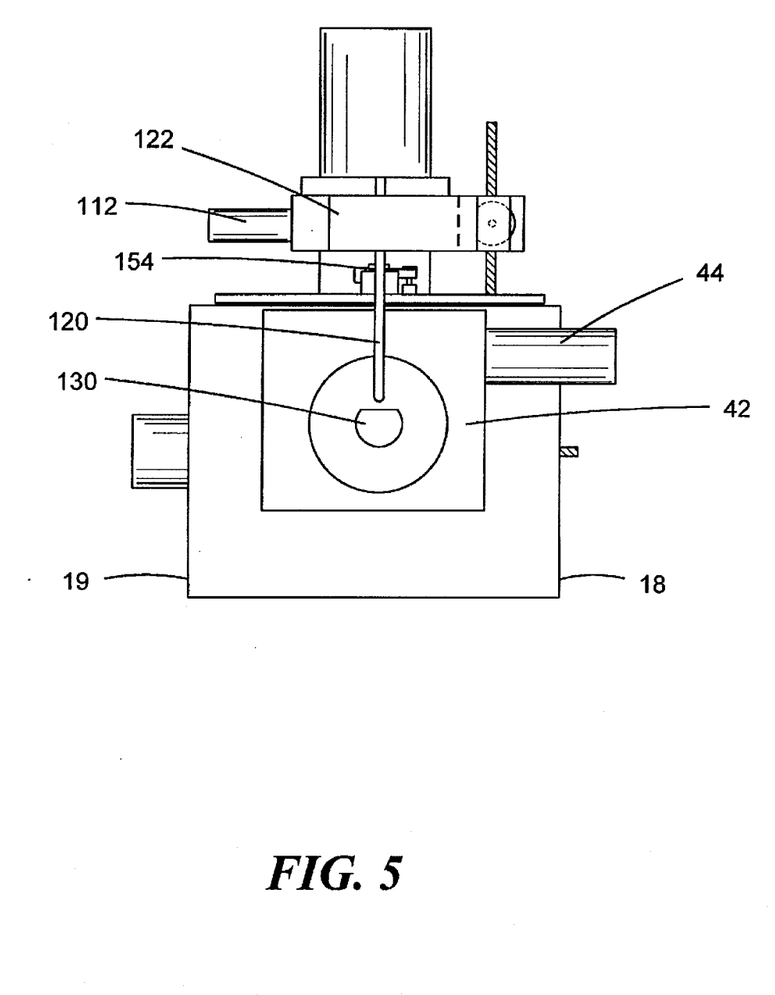
FIG. 5 is a left side view of an apparatus for measuring the radiation dose distribution embodying the present invention.

FIG. 5 shows a mechanical interlock aspect of the collision avoidance system. The system includes a phantom probe 120 mounted on a phantom probe support 122 coupled to probe support arm 80 and a phantom sensor 130 mounted on the cover 40 of the radiation measuring assembly 30 on the outside of the tank 12. The phantom probe 120 and the phantom sensor 130 are arranged in substantially the same relation as the probe 24 and radiation sensor 32. Preferably, the phantom probe 120 extends along an axis substantially parallel to the probe axis 28 and the phantom sensor 130 is disposed along the orientation axis 48. Because the phantom probe 120 is coupled to the probe support 80, the phantom probe 120 moves along a path parallel to that of the probe 24. The phantom sensor 130 is slightly larger than radiation sensor 32 and Solid Water enclosure 34 such that in the event of a collision, the phantom probe 120 will contact the phantom sensor 130 before the radiation probe 24 contacts enclosure 34. Preferably, the phantom probe 120 and the phantom sensor 130 have electrically conductive outer surfaces which are connected to the control system 160. The control system 160 can detect a collision by measuring a short circuit between the phantom probe 120 and the phantom sensor 130.

Figure 6:
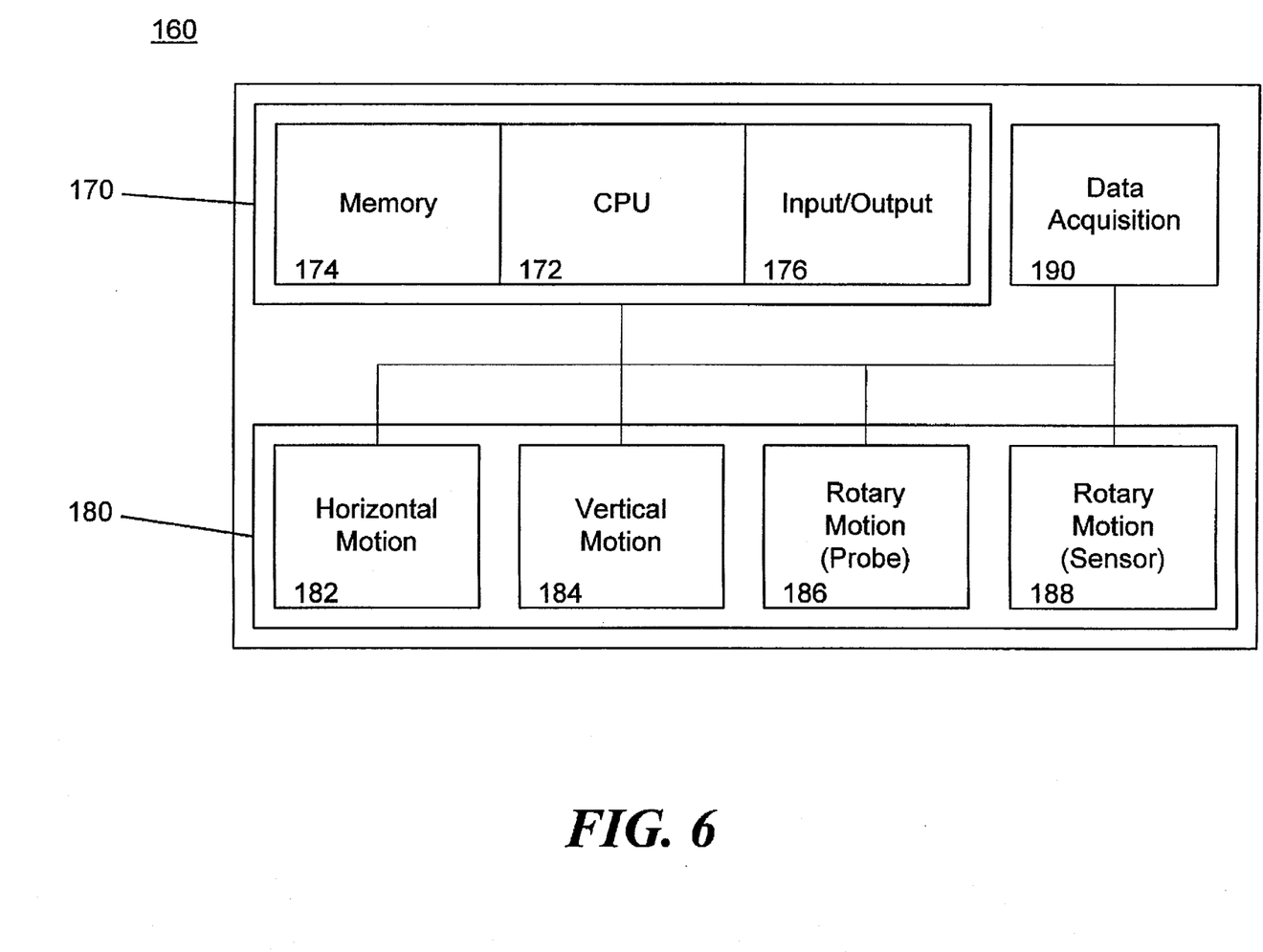
FIG. 6 is a diagrammatic view of the control system of an apparatus for measuring the radiation dose distribution embodying the present invention.

As shown in FIG. 6, the control system 160 includes a general purpose microcomputer including a CPU 172 with associated memory 174 and input/output 176 subsystems, a motion control system 180 and a data acquisition system 190. The motion control system 180 includes a horizontal motion control system 182 for controlling the horizontal actuator assembly 60, a vertical motion control system 184 for controlling the vertical actuator assembly 70, a source rotary motion control system 186 for controlling the source rotary actuator 110 and a sensor rotary motion control system 188 for controlling the source rotary actuator 42. The data acquisition system 190 is used to acquire the radiation dose data used by the control system 160 software to produce images of the radiation dose distribution.

Figure 7A:
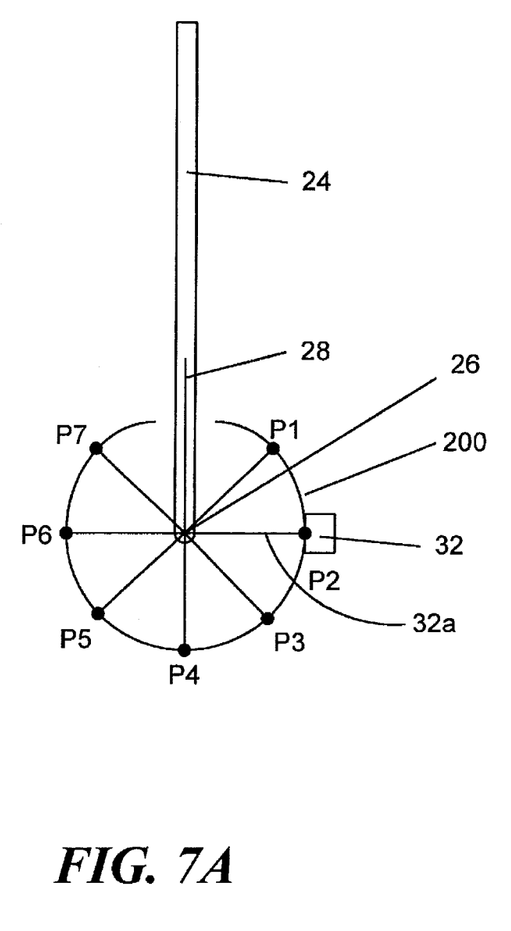
FIG. 7A is a diagrammatic view of the distal end of a radiation producing probe showing the path traveled by the radiation sensor with respect to the probe in accordance with one embodiment of the invention.

In operation, the probe 20 and sensor 32 are positioned as shown in FIG. 1. Then, the sensor assembly 30 is rotated about axis 48, so that sensor 32 effectively traverses path 200 as shown in FIG. 7A, with its sensing axis 32a always pointing to the source point 26. As this motion occurs, phantom apparatus 10 measures the radiation dose at a predetermined number of angular positions along the path 200, i.e. a path around the point source 26 in an Y-Z plane which extends along the probe axis 28. FIG. 7A shows a sequence of positions P1–P7 along the path 200 that the radiation sensor 32 subscribes about the point source 26 for a spherical radiation dose distribution. The radiation source 20 is then indexed about axis 28 by a predetermined angle and the process is repeated. The source 20 is further indexed about axis 28, and measurements are taken until the radiation source has been rotated 180 degrees. At this point in the process, control system 160 has measurements of the radiation dose over a spherical surface around the point source 26. By maintaining the ionization chamber 32 a constant distance from the point source between positions, the settling time of the ionization chamber is minimized. The process is then repeated for a series of concentric spheres to create a three dimensional map of the dose distribution. Where the radiation dose distribution is given a non-spherical shape, the phantom apparatus 10 can select points on the isodose contours of the dose distribution along a path that approximate the non-spherical shape. For example if the radiation dose distribution is produced in a cylindrical or even non-symmetrical shape about the probe axis, the control system 160 can be programmed to follow the contours of the given radiation isodose distribution.

The control system 160 carries out this process by positioning the radiation source 20 with respect to the ionization chamber 32 and then orienting the ionization chamber 32 to point directly at the point source 26 at the distal end of the radiation source 20 whereby the measurement axis 32a extends along a path that intersects the point source 26. The control system 160 then records the dose measured by the ionization chamber 32 and positions the radiation source 20 and the ionization chamber 32 for the next measurement. In the preferred embodiment, the rotary actuator 42 rotates the ionization chamber 32 about the orientation axis 48 and the opening of the ionization chamber 32 is disposed on the orientation axis 48. This simplifies the system computations because the distance from the point source to the ionization chamber 32 is not changed by the rotation of the ionization chamber 32. In the preferred embodiment, the control system 160 samples the ionization chamber 32 a predefined number of times and stores the average value. Preferably, the sample rate is three times per second and the value stored is the average of six values.

The control system 160 also plots the path of the probe 24 based on the input dose distribution geometry. Prior to moving the probe 24 to a given position, the control system 160 evaluates the path of the probe 24 with respect to the sensor 32 position to determine if they intersect or pass within a predetermined unsafe distance of each other, thus anticipating a collision. When a collision is predicted, the control system 160 plots a new path to avoid the collision.

Figure 7B:
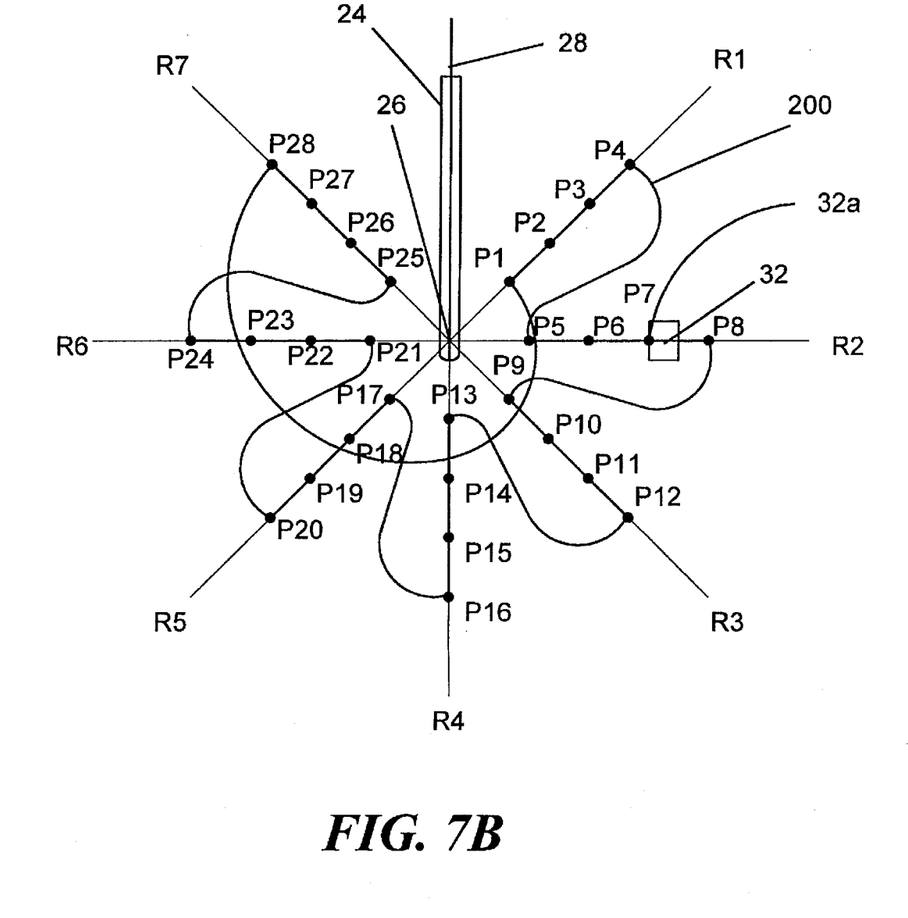
FIG. 7B is a diagrammatic view of the distal end of a radiation producing probe showing the path traveled by the radiation sensor with respect to the probe in accordance with an alternate embodiment of the invention.

FIG. 7B shows an alternate path 200 in accordance with a preferred embodiment of the invention. The system measures the radiation dose at predefined points P1–P28 along the path 200 about the source 20. In this embodiment, the path 200 is determined by input parameters for the polar coordinate system defined about the source point 26 of the radiation probe 24. The coordinates include the radial position, the sensor angle and source angle. The radial position is the distance along a radial path R1–R7 from the source point 26 to the ionization chamber 32. The sensor angle is the angle about the source point 26 of the radiation sensor or the angle of the radial path in a common plane with the axis of the probe 28. The source angle is the angle of the radiation source 24 about the axis of the probe 28. The input parameters for each coordinate include a start point, a stop point and an increment. In FIG. 7B, for example, the radial coordinates would be from P1 to P4 in (P4-P1)/3 increments; the sensor angle coordinates would be from R1 to R7 degrees in 45 degree increments; and the source angle coordinates (not shown) would be from 0 to 180 degrees in 45 degree increments. In the preferred embodiment, the radial coordinates are from 0.3 cm to 2 cm in 0.5 mm increments; the sensor angle coordinates would be from -90 to 90 degrees in 15 degree increments; and the source angle coordinates (not shown) would be from 0 to 180 degrees in 15 degree increments.

The path 200 of the ionization chamber 32 about the point source 26 from P1 to P28 is produced by nesting the motions with respect to each coordinate of the coordinate system. The inner most nested motion is the radial motion, for example, whereby the sensor moves from point P1 to point P4. The next nested motion is the sensor angle which is changed, for example, from R1 to R2. Note that the radial position starts at P5, the same radial distance as P1 and repeats for each new sensor angle. After sensor angle R7 is completed the ionization chamber 32 returns to P1 and the probe 24 is rotated about axis 28 and the process is repeated until the probe 24 is rotated 180 degrees. The result is a set of points representing dose values in a three dimensional space.

When the ionization chamber 32 is moved from one point to another, the system must wait for the ionization chamber 32 to settle before recording the dose value. In the preferred embodiment, the system continuously reads the ionization chamber 32 until the dose value is within one percent of the previous dose value. The system stores this reading and moves to the next position.

In the preferred embodiment, each of the motions is coordinated to prevent the ionization chamber 32 from contacting or crashing into the probe 24. This is accomplished by defining a path from a first point to a second point which essentially moves along all coordinate axes simultaneously and which maintains the radial distance between the ionization chamber 32 and probe 24 to be greater than or equal to the radial distance of second point irrespective of the sensor angle. For example, FIG. 7B shows the path from P28 to P1 to define a curved path which maintains the radial distance between the ionization chamber 32 and the probe 24 to be greater than the radial distance from the point source 26 to point P1 irrespective of the sensor angle.

Figure 8:
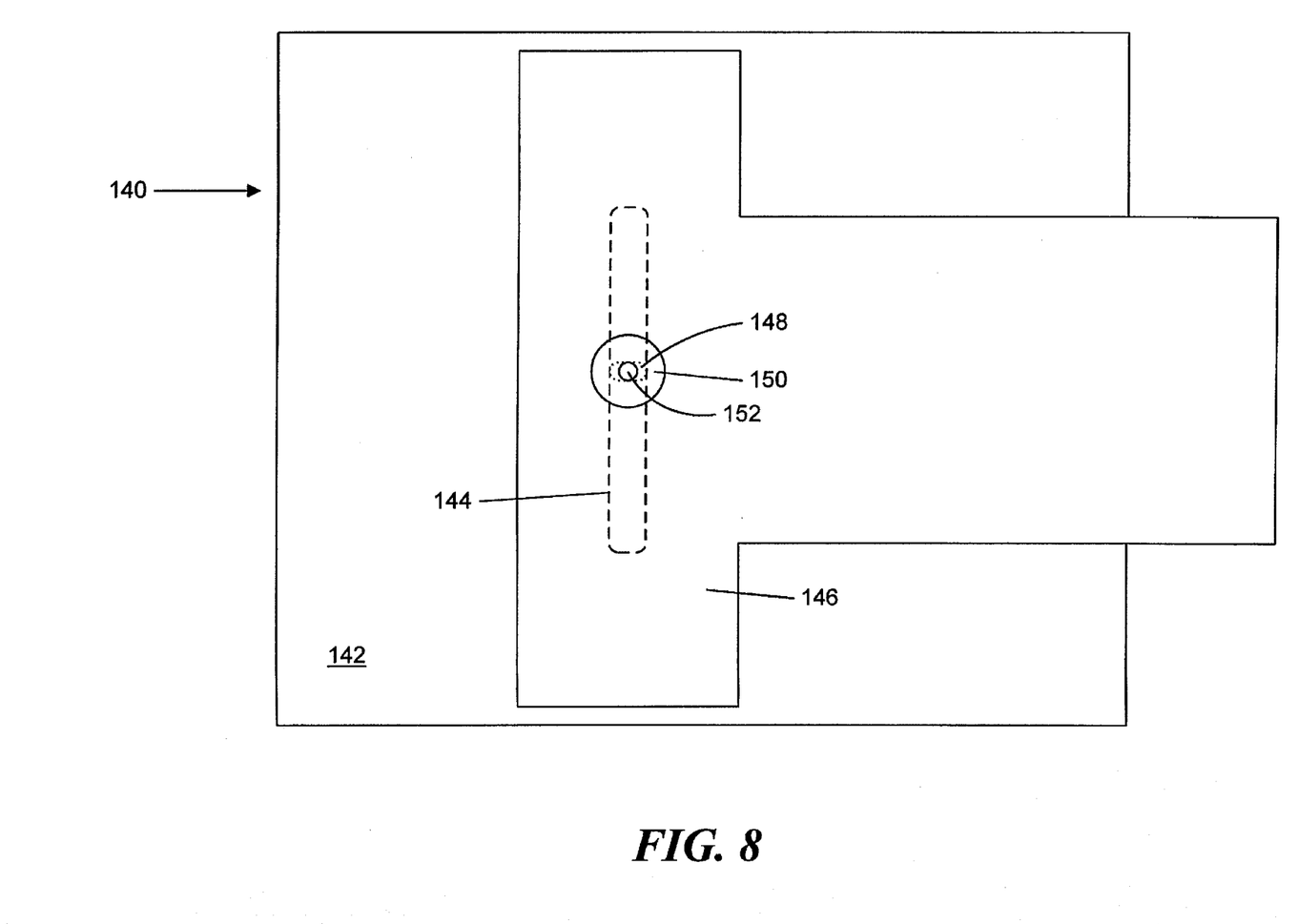
FIG. 8 is a detail view of the top cover and radiation shielding assembly of an apparatus for measuring radiation dose distribution embodying the present invention.

As shown in FIG. 8, the top cover of the water phantom includes radiation shielding assembly 140 which permits the probe to be inserted therethrough and positioned with respect to the radiation sensor 32 while effectively restricting the escape of radiation through the top cover. The shielding assembly 140 includes a top cover plate 142 having a transverse slot 144 extending therethrough, to allow the probe 24 to extend into the tank and to be moved within the area defined by the slot 144. The first shield plate 146 is provided to cover the slot 144 and includes an aperture 148 substantially the same cross sectional shape as the probe, through which the probe is inserted. The first shield plate 146 is coupled to the positioning system to move with the probe 24 and is sufficiently large enough to cover the slot 144 irrespective of the position of the probe 24 in the slot 144 and thereby preventing radiation from escaping through the slot 144.

Figure 9:
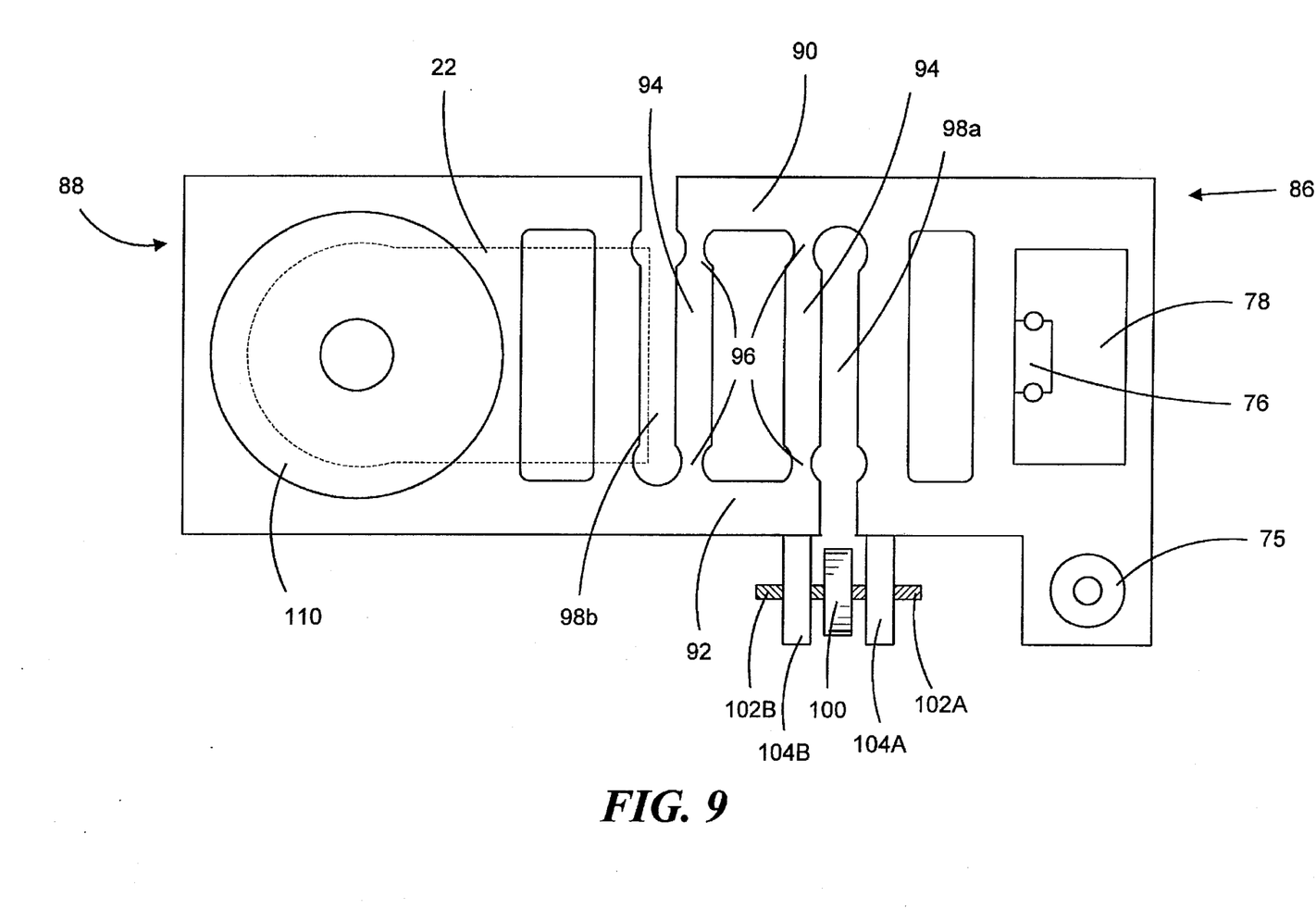
FIG. 9 is a detail view of the support arm of an apparatus for measuring radiation dose distribution embodying the present invention.

In the preferred embodiment, the support arm 80 includes an adjustable portion 84 which permits the position of probe axis 28 to be adjusted along the orientation axis 48 of the sensor assembly 30. Preferably, the probe axis 28 should lie in a plane that intersects the center of the radiation sensor 32. In the preferred embodiment, the plane should intersect the center of the aperture of the ionization chamber. This is accomplished by adjusting, either manually or automatically, the position of the probe axis 28 along the orientation axis 48 to provide peak output of the radiation sensor 32.

FIG. 9 shows a detail view of the support arm 80 extending along a support arm axis 82. The support arm 80 includes a base end 86 attached to vertical stage 78 separated from the free end 88 (where the radiation source 20 is mounted) by adjustable portion 84. In the preferred embodiment, the adjustable portion 84 comprises a parallelogram formed by base extension 90 and free end extension 92 connected to transverse support links 94 by flexible portions or flexures 96. The base extension 90 extends parallel to the support arm axis 82 from the base end 86 and the free end extension 92 extends parallel to the support arm axis 82 from the free end 88. In the nominal position, the transverse support links 94 extend substantially orthogonal to the base extension 90 and the free end extension 92. The transverse support links 94 and the flexible portions 96 permit the free end 88 and the free end extension 92 to move in a direction parallel to the support arm axis 82.

In the preferred embodiment, the adjustment is provided by an adjustment wheel 100 mounted on a pair of support blocks 104A and 104B on either side of cutout 98a. The adjustment wheel 100 includes a thread shaft 102 extending from both sides. One side of the adjustment wheel 100 includes a right handed external thread 102A that engages a right handed internal thread in support block 104A and the other side of the adjustment wheel 100 includes a left handed external thread 102B that engages a left handed internal thread in support block 104B. By turning the adjustment wheel 100 in the clockwise direction (as viewed from the side attached to the right hand threaded shaft 102A), the shaft forces the blocks 104A, 104B away from each other and extends the free end 88 away from the base end 86 along the support arm axis 82. Turning the adjustment wheel 100 in the counterclockwise direction brings the blocks 104A, 104B together and moves the free end 88 toward the base end 86. In an alternative embodiment, the threaded shaft 102 can be coupled to a servomotor controlled by control system 160 to provide automatic adjustment of the radiation source 20 position along the orientation axis 48.

In an alternative embodiment, the radiation source 20 can be positioned by a gantry positioning system mounted on top of the tank 12. This system could for example, be composed of a horizontal stage mounted on the top of the tank 12 with vertical and rotary actuators mounted thereon to provide vertical, horizontal and rotary movements. In yet another embodiment, the radiation source 20 can be supported by a robotic arm.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. An apparatus for measuring a radiation dose distribution at points disposed about a radiation source positioned in a tissue-equivalent volume, comprising:

a container defining an interior region for holding a tissue equivalent fluid medium, radiation measuring means disposed in said interior region for measuring radiation incident along a sensing axis, source positioning means for selectively positioning the radiation source within said interior region, sensor positioning means for selectively positioning said radiation measuring means within said interior region, control means for controlling said sensor positioning means and said source positioning means and to relatively position said radiation source with respect to said radiation measuring means wherein said sensing axis is directed substantially at said source at predetermined orientations about said source.

2. An apparatus according to claim 1, wherein said radiation measuring means is disposed along a first axis and said sensor positioning means includes a first rotation means for rotating said radiation measuring means about said first axis.

3. An apparatus according to claim 2, wherein said control means is operatively coupled to said sensor positioning means for rotating said radiation measuring means and said control means is operatively coupled to said source positioning means for controlling the movements of said radiation source relative to said radiation measuring means and wherein said control means further includes means for controlling said source positioning means to move said radiation source relative to said radiation measuring means along a predetermined path from a first predefined position to a second predefined position.

4. An apparatus according to claim 3, wherein said control means further includes means for rotating said radiation measuring means at each of said predefined positions to align said sensing axis to extend from said radiation measuring means to said radiation source.

5. An apparatus according to claim 3, wherein said control means further comprises means for preventing a collision between said radiation source and said radiation measuring means, said collision preventing means including means for moving said radiation measuring means along a predetermined path along a polar coordinate system.

6. An apparatus according to claim 3, wherein said control means further comprises means for preventing a collision between said radiation source and said radiation measuring means, said collision preventing means including means for comparing said predetermined path of said radiation source with respect to said radiation measuring means to determine an intersection of said predetermined path and said radiation measuring means and means for modifying said predetermined path upon the determination of an intersection.

7. An apparatus according to claim 2, further comprising third positioning means for positioning said radiation source along an axis substantially parallel to said first axis.

8. An apparatus according to claim 7, wherein said apparatus further includes said third positioning means coupling said radiation source to said source positioning means, said third positioning means comprising:

a base end portion coupled to said source positioning means and a free end portion separated from said base end portion along a second axis by an adjustable portion, said adjustable portion including a base extension extending from said base portion in a direction parallel to said second axis, a free extension extending from said free end portion in a direction parallel to said second axis, a pair of parallel spaced apart links extending substantially transverse to said base extension and said free extension, said parallel spaced apart links being coupled to said base extension and said free extension by compliant coupling means for permitting each of said links to pivot at said coupling, whereby said base extension and said free extension can move in a direction parallel to said second axis, and means for moving said free portion with respect to said base portion.

9. An apparatus according to claim 1, wherein said source positioning means includes second rotation means for rotating said radiation source about a source axis.

10. An apparatus according to claim 1, wherein said source positioning means includes means for moving said radiation source in at least one horizontal direction and a vertical direction.

11. An apparatus according to claim 1, further comprising:

Cover means for covering a top portion of said container means, said cover means including access means for permitting a portion of said radiation source to extend through said cover means into said medium and cover shielding means for preventing radiation from leaking out through said access means.

12. An apparatus according to claim 11, wherein said shielding means is coupled to said source positioning means and moves with said radiation source.

13. An apparatus according to claim 1, wherein said control means is operatively coupled to said source positioning means for controlling the movements of said radiation source relative to said radiation measuring means and said control means further includes means for controlling said source positioning means to move said radiation source relative to said radiation measuring means along a predetermined path from a first predefined position to a second predefined position.

14. An apparatus according to claim 13, wherein said radiation measuring means produces a signal representative of a radiation dose applied to a location in a portion of said medium, and said control means further includes means for recording said signal of said radiation measuring means at said predefined positions along said predetermined path.

15. An apparatus according to claim 14, wherein said control means further includes means for controlling the movements of said radiation source relative to said radiation measuring means along a predetermined path from said first predefined position to said second predefined position and for maintaining a substantially constant distance between said radiation source and said radiation measuring means during said movement of said radiation source from said first predefined position to said second predefined position.

16. An apparatus according to claim 1 further comprising means for preventing a collision between said radiation source and said radiation measuring means, said collision preventing means including a phantom radiation source means coupled to and extending in substantially parallel spaced relation to said radiation source and a phantom radiation measuring means coupled to and extending along a common axis with said radiation measuring means, said phantom radiation measuring means being sufficiently larger than said radiation measuring means whereby in the event of a collision, said phantom radiation source means contacts said phantom radiation measuring means before said radiation source contacts said radiation measuring means, and said phantom radiation measuring means and said phantom radiation source means include electrically conductive outer surfaces which are electrically coupled to said control means and said control means includes means for detecting an electrical short circuit between said phantom radiation measuring means and said phantom radiation source means and for stopping said sensor positioning means and said source positioning means to avoid a collision.

17. A method of measuring the radiation dose distribution of a radiation source used to apply a predefined dose of radiation to a target area, said radiation source including means for producing predefined radiation dose distribution geometries with respect to a predefined location in said target area, said method comprising the steps of:

A) positioning a radiation measuring device and said radiation source in a medium having a radiological equivalent characteristic of said target area, B) moving said radiation source with respect to said radiation measuring device along a predefined path from a first predefined position to at least one other predefined position C) recording the radiation dose at each of said predefined positions, and D) producing a representation of the radiation dose distribution about said radiation source.

18. A method according to claim 17 wherein step B further includes the sub-step of:

1) moving said radiation source with respect to said radiation measuring device along a predefined path corresponding to an expected radiation dose distribution geometry of said radiation source.

19. A method according to claim 18, wherein said predefined path follows an isodose contour of said radiation dose distribution.

20. A method according to claim 18, wherein said predefined path maintains said radiation measuring device at a substantially constant distance from said radiation source.

* * * * *